(12) United States Patent
Cho et al.

(10) Patent No.: US 11,285,087 B2
(45) Date of Patent: Mar. 29, 2022

(54) COSMETIC COMPOSITION HAVING INCREASED SKIN CONTACT AND MAKEUP PERSISTENCE AND METHOD OF MANUFACTURING SAME

(71) Applicant: COSMECCA KOREA CO., LTD., Chungcheongbuk-do (KR)

(72) Inventors: Hyun Dae Cho, Cheongju-si (KR); Byoung Moon Kim, Suwon-si (KR); Yeen Ji Kim, Seongnam-si (KR); Goo Ho Kwon, Gwangju-si (KR); Jin Young Kim, Seoul (KR)

(73) Assignee: COSMECCA KOREA CO., LTD., Chungcheongbuk-do (KR)

( * ) Notice: Subject to any disclaimer, the term of this patent is extended or adjusted under 35 U.S.C. 154(b) by 8 days.

(21) Appl. No.: 16/783,859

(22) Filed: Feb. 6, 2020

(65) Prior Publication Data

US 2020/0253840 A1  Aug. 13, 2020

(30) Foreign Application Priority Data

Feb. 11, 2019 (KR) ........................ 10-2019-0015460

(51) Int. Cl.
| | |
|---|---|
| *A61K 8/02* | (2006.01) |
| *A61K 8/25* | (2006.01) |
| *A61K 8/26* | (2006.01) |
| *A61K 8/27* | (2006.01) |
| *A61K 8/29* | (2006.01) |
| *A61K 8/81* | (2006.01) |
| *A61K 8/891* | (2006.01) |
| *A61K 8/58* | (2006.01) |
| *A61K 8/87* | (2006.01) |
| *A61K 8/88* | (2006.01) |
| *A61Q 1/06* | (2006.01) |
| *A61Q 1/10* | (2006.01) |

(52) U.S. Cl.
CPC .............. *A61K 8/022* (2013.01); *A61K 8/025* (2013.01); *A61K 8/25* (2013.01); *A61K 8/26* (2013.01); *A61K 8/27* (2013.01); *A61K 8/29* (2013.01); *A61K 8/585* (2013.01); *A61K 8/8141* (2013.01); *A61K 8/87* (2013.01); *A61K 8/88* (2013.01); *A61K 8/891* (2013.01); *A61Q 1/06* (2013.01); *A61Q 1/10* (2013.01); *A61K 2800/436* (2013.01); *A61K 2800/59* (2013.01)

(58) Field of Classification Search
None
See application file for complete search history.

(56) References Cited

U.S. PATENT DOCUMENTS

| | | | | |
|---|---|---|---|---|
| 2013/0236408 A1* | 9/2013 | Bui | ........................ | A61K 8/892 424/64 |
| 2018/0280256 A1* | 10/2018 | Watanabe | ................ | A61K 8/25 |

FOREIGN PATENT DOCUMENTS

| | | |
|---|---|---|
| KR | 10-0654062 B1 | 12/2006 |
| KR | 10-1050719 B1 | 7/2011 |
| KR | 10-2012-0026234 A | 3/2012 |
| KR | 10-2014-0069916 A | 6/2014 |
| KR | 10-2016-0102762 A | 8/2016 |
| KR | 10-1899024 B1 | 11/2018 |
| KR | 10-2018-0136315 A | 12/2018 |
| KR | 10-1928032 B1 | 12/2018 |

\* cited by examiner

*Primary Examiner* — David J Blanchard
*Assistant Examiner* — Sarah J Chickos
(74) *Attorney, Agent, or Firm* — Paratus Law Group, PLLC

(57) ABSTRACT

Disclosed are a cosmetic composition having increased skin contact and makeup persistence and a method of manufacturing the same. The method includes: forming a powder continuous phase by rapidly mixing a powder and a film-forming agent; and obtaining a cosmetic composition in which a surface of the powder is compounded with the film-forming agent by heating the powder continuous phase for a predetermined time. In an embodiment, the cosmetic composition is manufactured by the method. In an embodiment, the cosmetic composition includes 5 wt % to 30 wt % of a powder, 0.1 wt % to 10 wt % of a film-forming agent, 10 wt % to 30 wt % of a silicone oil, and 0.1 wt % to 10 wt % of a spherical powder.

6 Claims, 4 Drawing Sheets

COSMETIC COMPOSITION HAVING INCREASED SKIN CONTACT AND MAKEUP PERSISTENCE AND METHOD OF MANUFACTURING SAME

CROSS-REFERENCE TO RELATED APPLICATION

The present application claims priority to Korean Patent Application No. 10-2019-0015460, filed Feb. 11, 2019, which is hereby incorporated by reference in its entirety.

BACKGROUND

1. Technical Field

The present invention relates to a cosmetic composition having increased skin contact and makeup persistence and a method of manufacturing the same, and more particularly to a cosmetic composition having increased skin contact and makeup persistence using a formulation surface-treated with a modified silicone film-forming agent and a method of manufacturing the same.

2. Description of the Related Art

Women's interest in beauty is increasing consistently, but recently, women have taken growing interest in body care, beauty, and cosmetics to make themselves look more beautiful.

Men, as well as women, are interested in cosmetics for skin care, and thus the cosmetics market continues to expand, and various kinds of cosmetics are on the market.

In general, cosmetics may be broadly divided into basic cosmetics, makeup base, and color cosmetics, and are solid, liquid or gel cosmetics, and various cosmetic containers for storing the same have also been applied.

Recently, functional cosmetics that perform various functions such as moisturizing, whitening, anti-wrinkling, sun protection, acne relief, atopic relief, anti-inflammatory, keratolysis, etc. have been widely consumed.

These cosmetics have the functions of covering up and concealing defects of the skin and providing a beautiful color, that is, beautifying the skin, and of protecting the skin, such as skin nourishing, pore contraction and moisturizing and protection from UV rays, and moreover, may provide psychological stability through the skin beautification and skin protection functions.

General requirements for good cosmetics include ① natural color expression, ② good contact and persistence, ③ good use sensation, ④ prevention of clumping and smearing of makeup, and ⑤ high safety.

However, the general cosmetic composition has a problem of poor stability attributable to separation of the formulation due to sweating phenomena, such as generation of sweat or water droplets, because oily components escape to the surface of the formulation when the temperature changes rapidly to a high temperature. Hence, thorough research is ongoing into cosmetic compositions, capable of achieving a superior use sensation from the aspects of persistence, contact and uniform spreading, reducing sweating, and satisfying all of floating, spreading, contact and persistence.

In particular, a conventional powder included in the cosmetics is coated with fatty acid, ester or pure silicone oil, and thus the persistence of makeup may deteriorate and the effect thereof may not last long, which is undesirable.

Therefore, there is a need for a cosmetic composition having increased skin contact and makeup persistence by solving these problems.

SUMMARY

Accordingly, exemplary embodiments of the present invention are intended to provide a cosmetic composition having increased skin contact and makeup persistence using a formulation surface-treated with a modified silicone film-forming agent.

In addition, exemplary embodiments of the present invention are intended to provide a cosmetic composition having increased persistence and contact and superior powder dispersibility to thus impart a good use sensation to a user.

In addition, exemplary embodiments of the present invention are intended to provide a cosmetic composition that enables high-quality makeup to be maintained for a long time by overcoming problems in which makeup does not last long.

An aspect of the present invention provides a method of manufacturing a cosmetic composition having increased skin contact and makeup persistence, the method including forming a powder continuous phase by rapidly mixing a powder and a film-forming agent, and obtaining a cosmetic composition in which the surface of the powder is compounded with the film-forming agent by heating the powder continuous phase for a predetermined time.

The method of the present invention may further include homogenizing the cosmetic composition through pulverization and filtration.

Here, the forming the powder continuous phase may include rapidly mixing 90 wt % to 99.5 wt % of the powder and 0.5 wt % to 10 wt % of the film-forming agent.

The obtaining the cosmetic composition may include performing heating at a reaction temperature of 60° C. to 120° C. for 0.5 hr to 24 hr.

The homogenizing may include performing pulverization using a pulverizer of 3HP or more and filtration with 20 to 100 mesh.

The forming the powder continuous phase may include forming a first powder continuous phase activated with a weakly acidic region by placing 90 wt % to 99.5 wt % of the powder relative to 1 kg of the total amount in a reactor, followed by addition with a powder activation solvent with stirring at 300 rpm to 700 rpm, and forming a second powder continuous phase by adding the first powder continuous phase with 0.5 wt % to 10 wt % of the film-forming agent with stirring at 200 rpm to 400 rpm.

The powder may be at least one selected from the group consisting of talc, kaolin, mica, sericite, nylon-12, methyl methacrylate crosspolymer, polymethyl methacrylate, boron nitride, alumina, titanium dioxide, zinc oxide, iron oxide, silica, pearl, organic dye, lake pigment, organic pigment and mixtures thereof.

The film-forming agent may be at least one selected from the group consisting of modified silicones, including acrylate/dimethicone copolymer, acrylate/stearyl acrylate/dimethicone methacrylate copolymer, acrylate/ethylhexyl acrylate/dimethicone methacrylate copolymer, trimethylsiloxysilicate/dimethiconol crosspolymer and mixtures thereof.

Another aspect of the present invention provides a cosmetic composition having increased skin contact and makeup persistence, manufactured by the above method.

Still another aspect of the present invention provides a cosmetic composition having increased skin contact and makeup persistence, including 5 wt % to 30 wt % of a powder, 0.1 wt % to 10 wt % of a film-forming agent, 10 wt % to 30 wt % of a silicone oil, and 0.1 wt % to 10 wt % of a spherical powder.

The silicone oil may be at least one selected from the group consisting of cyclopentasiloxane, cyclohexasiloxane, dimethicone, phenyl trimethicone, capryl dimethicone, diphenyl dimethicone and mixtures thereof.

The spherical powder may be at least one selected from the group consisting of silica, polyurethane, polymethyl methacrylate, nylon, silicone resin powder and mixtures thereof.

The cosmetic composition may further include at least one active principle, the active principle including at least one selected from the group consisting of a natural extract, oil, moisturizer, whitening agent, anti-wrinkling agent, acne reliever, atopy reliever, sunscreen, hair growth promoter, vitamin and derivative thereof, amino acid, polypeptide, anti-inflammatory agent, female hormone agent, keratolytic agent, disinfecting agent, placenta, allantoin, yeast extract, collagen, elastin, DHA, EPA, ceramide, perfume and mixtures thereof.

Yet another aspect of the present invention provides a cosmetic product, including the above cosmetic composition.

The cosmetic product may be at least one selected from the group consisting of a BB cream, foundation, makeup base, primer, concealer, sun cream, lipstick, lip gloss, tint, powder, blush, eyeshadow, eyeliner, and mascara.

According to exemplary embodiments of the present invention, a cosmetic composition can be imparted with increased skin contact and makeup persistence due to the use of a formulation surface-treated with a modified silicone film-forming agent.

Also, according to exemplary embodiments of the present invention, the cosmetic composition has increased persistence and contact and superior powder dispersibility, thus imparting a good use sensation to a user.

Also, according to exemplary embodiments of the present invention, the cosmetic composition enables high-quality makeup to be maintained for a long time by overcoming problems in which makeup does not last long.

DETAILED DESCRIPTION

Figure 1:
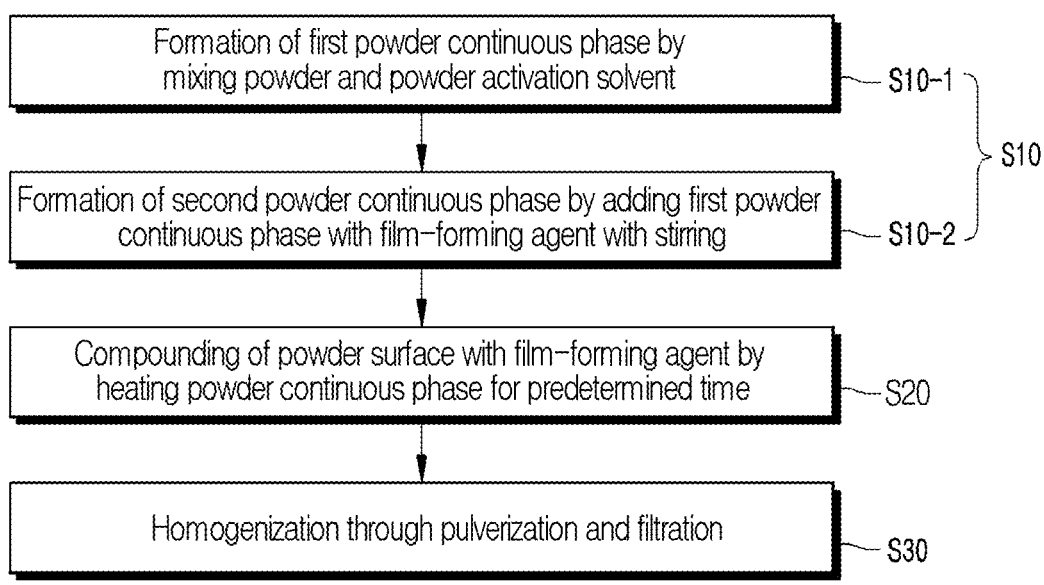
FIG. 1 is a flowchart showing a process of manufacturing a cosmetic composition having increased skin contact and makeup persistence according to an embodiment of the present invention.

Hereinafter, a detailed description will be given of preferred embodiments of the present invention with reference to the appended drawings. However, the present invention is not limited to the embodiments described herein but may be embodied in other forms. Rather, the embodiments introduced herein are provided so that the disclosure may be made thorough and complete and so as to fully convey the spirit of the present invention to those skilled in the art. Throughout the specification, like reference numerals refer to like elements.

Figure 2A:
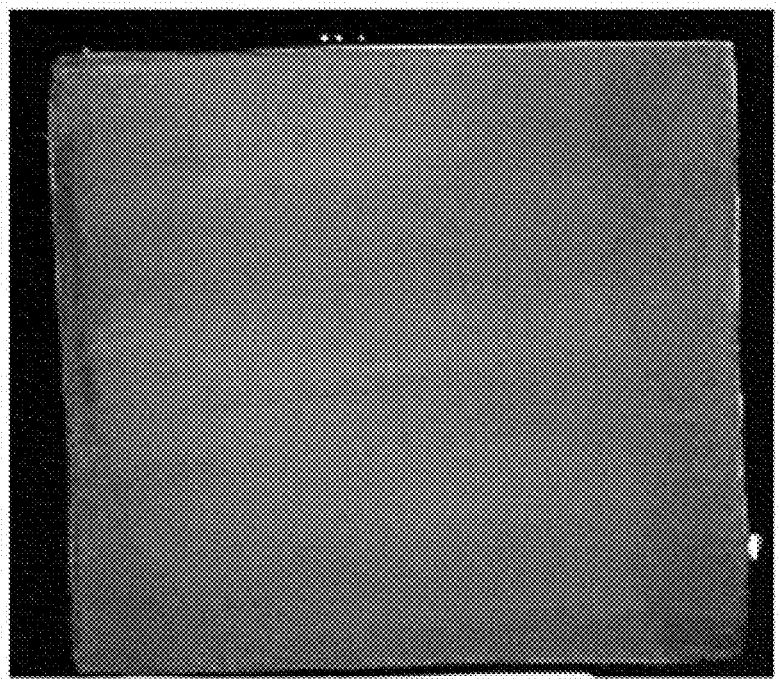
FIGS. 2A and 2B are images before and after adhesion testing of the cosmetic composition having increased skin contact and makeup persistence of Example 1 of the present invention using a coating adhesion test tape.
Figure 2B:
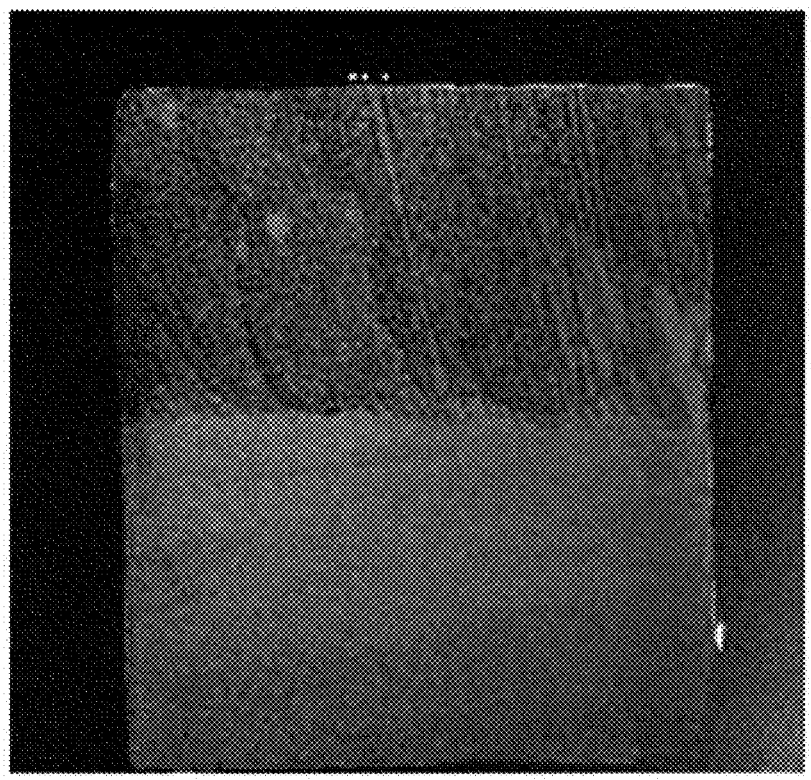
Figure 3A:
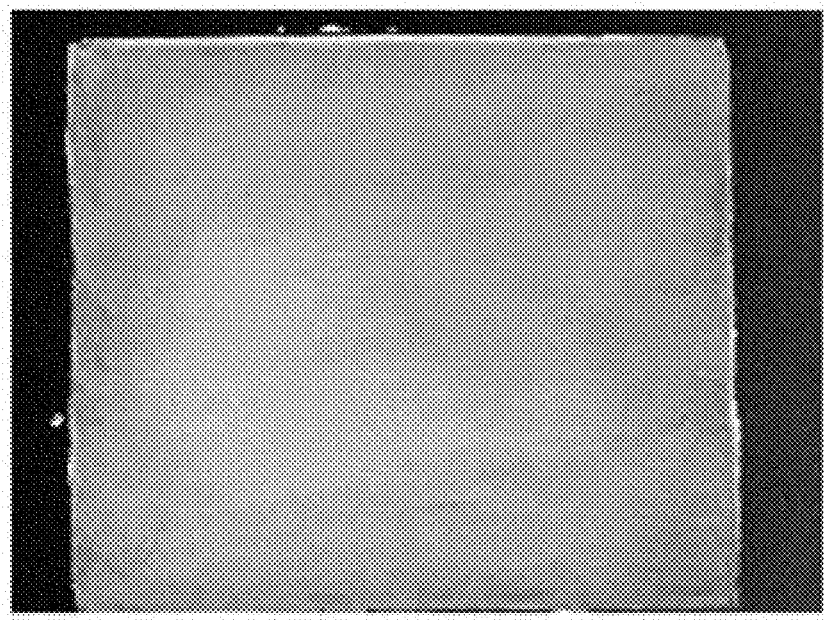
FIGS. 3A and 3B are images before and after adhesion testing of the cosmetic composition having increased skin contact and makeup persistence of Example 2 of the present invention using a coating adhesion test tape.
Figure 3B:
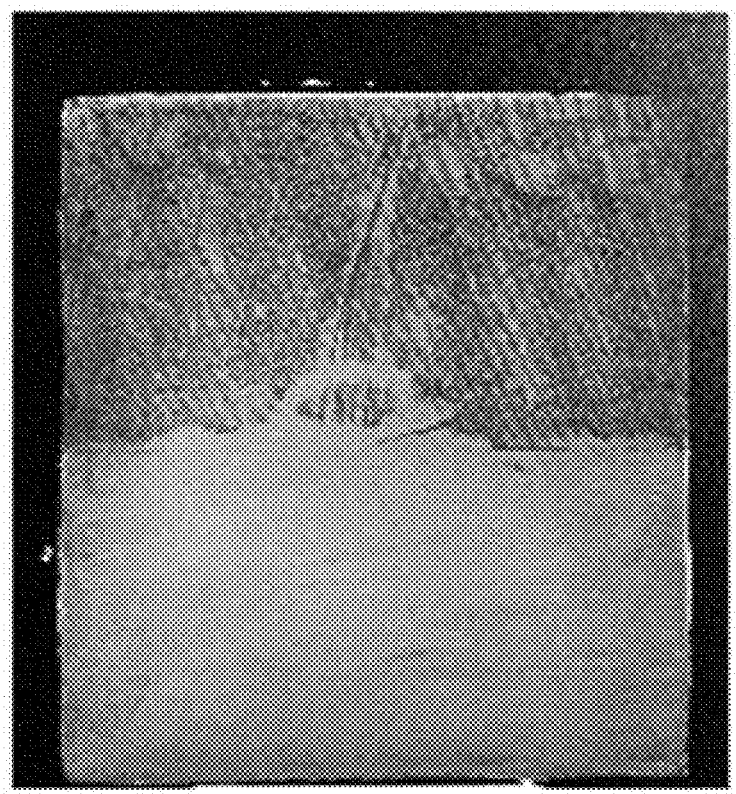
Figure 4A:
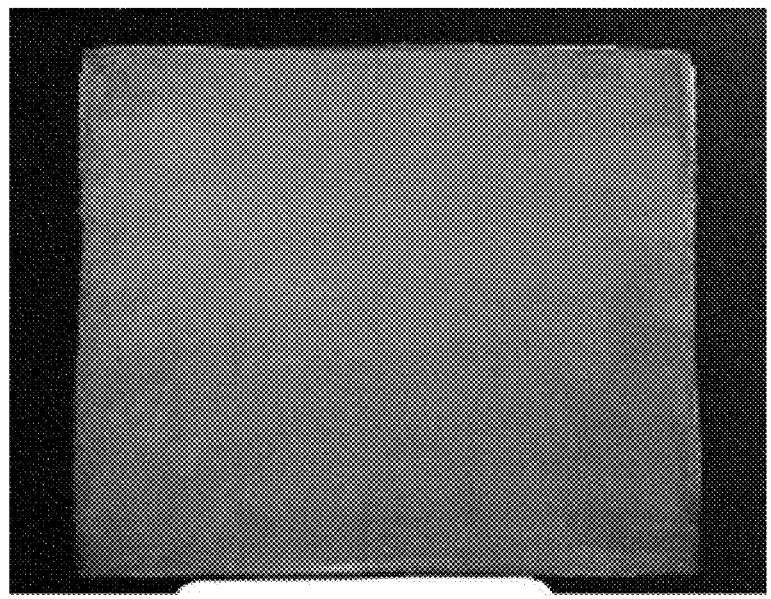
FIGS. 4A and 4B are images before and after adhesion testing of the cosmetic composition having increased skin contact and makeup persistence of Comparative Example 1 of the present invention using a coating adhesion test tape.
Figure 4B:
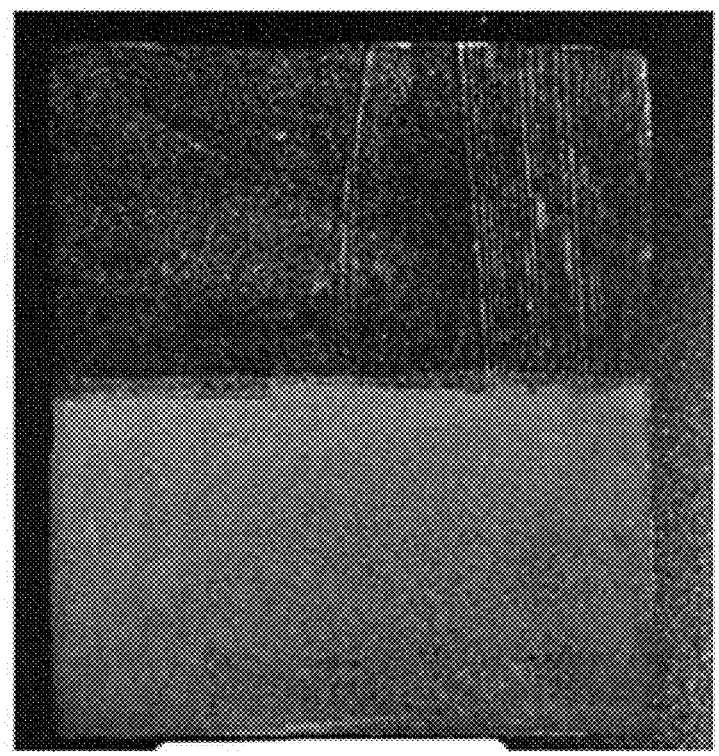

FIG. 1 is a flowchart showing a process of preparing a cosmetic composition having increased skin contact and makeup persistence according to an embodiment of the present invention, FIGS. 2A and 2B are images before and after adhesion testing of the cosmetic composition having increased skin contact and makeup persistence of Example 1 of the present invention using a coating adhesion test tape, FIGS. 3A and 3B are images before and after adhesion testing of the cosmetic composition having increased skin contact and makeup persistence of Example 2 of the present invention using a coating adhesion test tape, and FIGS. 4A and 4B are images before and after adhesion testing of the cosmetic composition having increased skin contact and makeup persistence of Comparative Example 1 of the present invention using a coating adhesion test tape.

With reference to FIGS. 1, 2A and 2B to 4A and 4B, the method of manufacturing the cosmetic composition having increased skin contact and makeup persistence according to an embodiment of the present invention may include forming a powder continuous phase by rapidly mixing a powder and a film-forming agent (S10), obtaining a cosmetic composition in which the surface of the powder is compounded with the film-forming agent by heating the powder continuous phase for a predetermined time (S20), and homogenizing the cosmetic composition through pulverization and filtration (S30).

According to the present invention, at least one powder is surface-treated with a modified silicone film-forming agent, thereby obtaining a powder coating composition having superior skin contact and makeup persistence.

The cosmetic composition of the present invention is able to increase skin contact and makeup persistence of a powder for use in, for example, a BB cream, foundation, makeup base, primer, concealer, sun cream, lipstick, lip gloss, tint, powder, blush, eyeshadow, eyeliner, mascara, or the like.

Specifically, a powder such as a white pigment, a color pigment, a pearl pigment, an extender, etc. is coated with a particularly polymerized modified silicone film-forming agent, thereby increasing skin contact and ultimately makeup persistence.

Thereby, problems with a conventional powder, in which makeup persistence is lowered and the effect thereof does not last long, due to coating with fatty acid, ester or pure silicone oil, may be overcome.

Specifically, a powder and a film-forming agent are rapidly mixed, thus forming a powder continuous phase (S10). Here, the forming the powder continuous phase (S10) may be conducted by rapidly mixing 90 wt % to 99.5 wt % of the powder with 0.5 wt % to 10 wt % of the film-forming agent.

The forming the powder continuous phase (S10) may include forming a first powder continuous phase activated with a weakly acidic region by placing 90 wt % to 99.5 wt % of the powder relative to 1 kg of the total amount in a reactor, followed by addition with a powder activation solvent with stirring at 300 rpm to 700 rpm (S10-1), and forming a second powder continuous phase by adding the first powder continuous phase with 0.5 wt % to 10 wt % of the film-forming agent with stirring at 200 rpm to 400 rpm (S10-2).

Specifically, the powder is placed in an amount of 90 wt % to 99.5 wt % relative to 1 kg of the total amount in the reactor, and added with the powder activation solvent with stirring at 300 rpm to 700 rpm, thus forming a first powder continuous phase activated with a weakly acidic region (S10-1).

Then, the first powder continuous phase surface-activated with cations is slowly added with 0.5 wt % to 10 wt % of a modified silicone film-forming agent with stirring at 200 rpm to 400 rpm, thus forming a second powder continuous phase (S10-2).

Here, if the amount of the modified silicone film-forming agent is less than 0.1 wt %, skin contact and makeup persistence may become insignificant. On the other hand, if the amount of the modified silicone film-forming agent exceeds 10 wt %, power dispersibility and use sensation may decrease. Hence, it is preferred that the amount of the film-forming agent that is added fall within the above range.

Thereafter, the powder continuous phase is heated for a predetermined time, thus obtaining a cosmetic composition in which the powder surface is compounded with the film-forming agent (S20). Here, the obtaining the cosmetic composition may be performed under heating conditions of a reaction temperature of 60° C. to 120° C. for 0.5 hr to 24 hr.

Thereafter, the cosmetic composition is pulverized and filtered and thus homogenized (S30). Here, the homogenization step (S30) may be performed through pulverization using a pulverizer of 3HP or more and filtration with 20 to 100 mesh.

In the present invention, the powder may include at least one selected from the group consisting of talc, kaolin, mica, sericite, nylon-12, methyl methacrylate crosspolymer, polymethyl methacrylate, boron nitride, alumina, titanium dioxide, zinc oxide, iron oxide, silica, pearl, organic dye, lake pigment, organic pigment and mixtures thereof.

The film-forming agent may include at least one selected from the group consisting of modified silicones, such as acrylate/dimethicone copolymer, acrylate/stearyl acrylate/dimethicone methacrylate copolymer, acrylate/ethylhexyl acrylate/dimethicone methacrylate copolymer, trimethylsiloxysilicate/dimethiconol crosspolymer and mixtures thereof.

The actual component ratio of a cosmetic composition manufactured by the above method and the manufacturing process thereof are described in detail below.

According to an embodiment of the present invention, the cosmetic composition having increased skin contact and makeup persistence may include 5 wt % to 30 wt % of a powder, 0.1 wt % to 10 wt % of a film-forming agent, 10 wt % to 30 wt % of a silicone oil and 0.1 wt % to 10 wt % of a spherical powder.

Specific examples and comparative examples of the cosmetic composition are shown in Table 1 below.

TABLE 1

| Phase | Component | Example 1 (wt %) | Example 2 (wt %) | Comparative Example 1 (wt %) |
|---|---|---|---|---|
| Pigment (A) | 1. Titanium dioxide (Powder) | 9.7 | 19.4 | 9.7 |
| | 2. Trimethylsiloxysilicate/dimethiconol crosspolymer (Film-forming agent) | 0.3 | 0.6 | |
| | 3. Triethoxycaprylylsilane (Coating agent) | | | 0.3 |

TABLE 1-continued

| Phase | Component | Example 1 (wt %) | Example 2 (wt %) | Comparative Example 1 (wt %) |
|---|---|---|---|---|
| | 4. Iron oxide (Pigment) | 2 | 2 | 2 |
| Oil part (B) | 5. Cyclopentasiloxane (Silicone oil) | 20 | 20 | 20 |
| | 6. Quaternium-18 Bentonite (Thickener) | 0.95 | 0.95 | 0.95 |
| | 7. Silica (Spherical powder) | 0.5 | 0.5 | 0.5 |
| | 8. PEG-10 dimethicone (Emulsifier) | 3 | 3 | 3 |
| Aqueous part (C) | 9. Disodium EDTA (Sequestering agent) | 0.05 | 0.05 | 0.05 |
| | 10. Sodium chloride (Emulsion stabilizer) | 1.5 | 1.5 | 1.5 |
| | 11. Butylene glycol (Moisturizer) | 5 | 5 | 5 |
| | 12. Potassium sorbate (Preservative) | 0.11 | 0.11 | 0.11 |
| | 13. Sodium benzoate (Preservative) | 0.22 | 0.22 | 0.22 |
| | 14. Purified water | 56.57 | 46.57 | 56.57 |
| Additive (D) | 15. Perfume | 0.1 | 0.1 | 0.1 |

The cosmetic composition having increased skin contact and makeup persistence according to an embodiment of the present invention was manufactured using components in the amounts shown in Table 1. The specific manufacturing process thereof is described below.

Specifically, a pigment (A) including component 1 to component 4 shown in Table 1 was placed in a Henschel mixer and pulverized and mixed at 800 rpm to 1,000 rpm at room temperature for 5 min to afford a mixture. The mixture and an oil part (B) including component 5 to component 8 shown in Table 1 were placed in a stirring vacuum emulsification bath, warmed to 70° C. to 80° C. with stirring, and uniformly mixed with stirring at 1,500 rpm to 2,600 rpm for 5 min to 10 min using a homo mixer. Here, the powder was sufficiently stirred before introduction into the vacuum emulsification bath.

An aqueous part (C) was placed in an aqueous dissolution bath enabling temperature adjustment and stirring, and was uniformly mixed with stirring at a temperature of 60° C. to 70° C. Then, the aqueous part of the aqueous dissolution bath was added to the oil part of the vacuum emulsification bath, mixed with stirring at 1,500 rpm to 3,600 rpm for 5 min to 8 min using a homo mixer, and then cooled to 40° C. to 45° C.

Thereafter, an additive (D) was added at about 40° C. to 45° C. and uniformly mixed with stirring. Moreover, mixing was performed with stirring at 1,500 rpm to 3,600 rpm for 2 min to 3 min using a homo mixer at 30° C. to 35° C. in the vacuum emulsification bath. After stirring, cooling to 30° C. to 35° C. was performed, finally obtaining BB cream.

As described above, the powder in an embodiment of the present invention may be a planar powder, the amount of which may be, based on the total weight of the composition, 5 wt % to 30 wt %, preferably 5 wt % to 25 wt %, and more preferably 5 wt % to 20 wt %. If the amount of the powder is less than 5 wt %, the persistence may decrease. On the other hand, if the amount thereof exceeds 30 wt %, payoff may decrease. Hence, it is preferred that the wt % amount of the powder that is added be determined within the above range.

In the present invention, the amount of the film-forming agent is preferably 0.1 wt % to 10 wt %. If the amount thereof is less than 0.1 wt %, the persistence may decrease. On the other hand, if the amount thereof exceeds 10 wt %, payoff may decrease. Hence, it is preferred that the amount of the film-forming agent that is added be determined within the above range.

In the present invention, the amount of the silicone oil may be 10 wt % to 30 wt %, preferably 10 wt % to 25 wt %, and more preferably 12 wt % to 20 wt %. If the amount of the silicone oil is less than 10 wt %, the relative amount of the powder may increase and dry and transfer effects may decrease. On the other hand, if the amount thereof exceeds 30 wt %, persistence may decrease. Hence, it is preferred that the amount of the silicone oil that is added be determined within the above range.

Here, the silicone oil that is added may include at least one selected from the group consisting of cyclopentasiloxane, cyclohexasiloxane, dimethicone, phenyl trimethicone, capryl dimethicone, diphenyl dimethicone and mixtures thereof.

The amount of the spherical powder may be, based on the total weight of the composition, 0.1 wt % to 10 wt %, and preferably 0.1 wt % to 5 wt %. If the amount of the spherical powder is less than 0.1 wt %, payoff may decrease. On the other hand, if the amount thereof exceeds 10 wt %, skin contact may decrease. Hence, it is preferred that the amount of the spherical powder that is added be determined within the above range.

Here, the spherical powder may include at least one selected from the group consisting of silica, polyurethane, polymethyl methacrylate, nylon, silicone resin powder and mixtures thereof.

As described above, the cosmetic composition manufactured above is homogenized through pulverization and filtration (S30). The reason why the homogenization process (S30) is performed is that the powder has an oxygen system in its basic structure and aggregates with electrostatic attraction, making it possible to achieve high quality with more uniform particles after filtration.

A sensory evaluation of 10 persons for the skin contact was performed using the cosmetic composition having increased skin contact and makeup persistence of each of Examples 1 and 2 and Comparative Example 1. The higher the score, the better the skin contact, and the scores are higher in the order of Example 2, Example 1, and Comparative Example 1, from which the skin contact was evaluated to improve with an increase in the amount of the film-forming agent.

* Contact sensory test      <5 out of 5>

TABLE 2

| Subject | Example 1 | Example 2 | Comparative Example 1 |
|---|---|---|---|
| 1 | 4.2 | 4.5 | 3.8 |
| 2 | 4.1 | 4.3 | 3.6 |
| 3 | 3.6 | 3.8 | 4.3 |
| 4 | 3.8 | 4.4 | 4 |
| 5 | 4.2 | 3.8 | 3.9 |
| 6 | 3.9 | 4.4 | 4 |
| 7 | 4.4 | 4.6 | 3.6 |
| 8 | 3.8 | 3.7 | 4 |
| 9 | 4 | 3.8 | 3.3 |
| 10 | 4.2 | 4.4 | 3.6 |
| Average | 4.02 | 4.17 | 3.81 |

Moreover, a sensory evaluation of 10 persons for the transfer was performed with Examples 1 and 2 and Comparative Example 1. The lower the score, the lower the transfer, and the scores are lower in the order of Example 2, Example 1, and Comparative Example 1, from which the transfer was evaluated to be decreased with an increase in the amount of the film-forming agent.

* Transfer sensory test      <5 out of 5>

TABLE 3

| Subject | Example 1 | Example 2 | Comparative Example 1 |
|---|---|---|---|
| 1 | 3.6 | 3 | 3.4 |
| 2 | 3.4 | 3.6 | 4 |
| 3 | 3.6 | 3.3 | 4 |
| 4 | 4 | 3.2 | 3 |
| 5 | 3.4 | 3.8 | 4.2 |
| 6 | 3.6 | 3.4 | 4 |
| 7 | 3.3 | 3 | 3.9 |
| 8 | 3.5 | 2.8 | 3.6 |
| 9 | 3.3 | 3 | 3.6 |
| 10 | 3.2 | 2.8 | 3.4 |
| Average | 3.49 | 3.19 | 3.71 |

0.02 g of each sample was applied on a substrate 50 mm×50 mm in size, dried for 20 min, and then subjected to an adhesion test using a 3M 610 coating adhesion test tape.

FIGS. 2A and 2B are images before and after the adhesion test of the cosmetic composition having increased skin contact and makeup persistence of Example 1 using a coating adhesion test tape, FIGS. 3A and 3B are images before and after the adhesion test of the cosmetic composition having increased skin contact and makeup persistence of Example 2 using a coating adhesion test tape, and FIGS. 4A and 4B are images before and after the adhesion test of the cosmetic composition having increased skin contact and makeup persistence of Comparative Example 1 using a coating adhesion test tape.

When viewed with the naked eye, most of the sample remained for Example 2, followed sequentially by Example 1 and Comparative Example 1, and the sample was found to have better adhesion in Examples than in Comparative Example.

The cosmetic composition having increased skin contact and makeup persistence according to an embodiment of the present invention may further include at least one active principle.

Specifically, the active principle may include at least one selected from the group consisting of natural extract, oil, moisturizer, whitening agent, anti-wrinkling agent, acne reliever, atopy reliever, sunscreen, hair growth promoter, vitamin and derivatives thereof, amino acid, polypeptide, anti-inflammatory agent, female hormone agent, keratolytic agent, disinfecting agent, placenta, allantoin, yeast extract, collagen, elastin, DHA, EPA, ceramide, perfume and mixtures thereof.

In the active principle, the oil may include at least one selected from the group consisting of fat and oil, wax, hydrocarbon oil, fatty acid ester oil, alcohol oil, butter, silicone oil, ester oil and mixtures thereof.

Specifically, the fat and oil may include at least one selected from the group consisting of macadamia nut oil, olive oil, jojoba oil, almond oil, apricot seed oil, green tea oil, meadowfoam oil, sunflower oil, argan oil, camellia oil, avocado oil, soybean oil, grape seed oil, castor oil, rice bran oil and mixtures thereof.

The wax may include at least one selected from the group consisting of carnauba wax, candelilla wax, jojoba oil, beeswax, lanolin, soybean wax, rice wax, silicone wax and mixtures thereof.

The hydrocarbon oil may include at least one selected from the group consisting of liquid paraffin, paraffin, Vaseline, ceresin, microcrystalline wax, squalane and mixtures thereof.

The fatty acid ester oil may include at least one selected from the group consisting of lauric acid, myristic acid, palmitic acid, stearic acid, isostearic acid and mixtures thereof, and the alcohol oil may include at least one selected from the group consisting of cetyl alcohol, stearyl alcohol, isostearyl alcohol, 2-octyldodecyl, 2-ethylhexanecetyl, diisostearyl malate and mixtures thereof.

The butter may include at least one selected from the group consisting of shea butter, soy butter, mango butter and mixtures thereof.

The silicone oil may include at least one selected from the group consisting of dimethicones, cyclomethicones, silicone polymers and mixtures thereof.

The ester oil may include at least one selected from the group consisting of cetyl ethyl hexanoate, diglyceryl triisostearate, capric/caprylic triglyceride, glyceryl tri-2-ethylhexanoate, isononyl isononanoate, ethylhexyl isononanoate, ethylhexyl palmitate, isostearyl isostearate, neopentyl glycol dicaprate, neopentyl glycol diethylhexanoate, octyldodecyl myristate, pentaerythrityl tetraethylhexanoate, pentaerythrityl tetraisostearate, isotridecyl isononanoate, trimethylolpropane triisostearate, squalane and mixtures thereof.

In the active principle, the moisturizer may include at least one selected from the group consisting of sodium lactate, hydroproline, sodium 2-phytolipo-5-carbonate, hyaluronic acid, sodium hyaluronate, ceramide, phytosterol, cholesterol, sitosterol and mixtures thereof.

In the active principle, the sunscreen may include at least one selected from the group consisting of benzophenone derivatives, para-aminobenzoic acid derivatives, methoxy cinnamic acid derivatives, salicylic acid derivatives and mixtures thereof.

In the active principle, the whitening agent may include at least one selected from the group consisting of arbutin and arbutin derivatives, kojic acid, vitamin C and vitamin C derivatives, and mixtures thereof.

In the active principle, the hair growth promoter may include at least one of a blood circulation promoter and a topical stimulant. Here, the blood circulation promoter may include at least one selected from the group consisting of moonshine weed extract, cepharanthine, vitamin E and derivatives thereof, gamma-oryzanol, proteoglycan and mixtures thereof.

Also, the topical stimulant in the hair growth promoter may include at least one selected from the group consisting of pepper tincture, ginger tincture, cantharis tincture, nicotinic acid benzyl ester and mixtures thereof.

In the active principle, the vitamin and derivatives thereof are not particularly limited, but may include at least one selected from the group consisting of vitamin A and derivatives thereof, vitamin B1, B2, B6, E and derivatives thereof, vitamin D, H, K, pantothenic acid and derivatives thereof, biotin, panthenol and mixtures thereof.

In the active principle, the amino acid may include at least one selected from the group consisting of cystine, cysteine, methionine, serine, leucine, tryptophan, amino acid extract, EGF (Epidermal Growth Factor), IGF (Insulin-like Growth Factor), FGF (Fibroblast Growth Factor), kappa-peptide and mixtures thereof.

In the active principle, the anti-inflammatory agent may include at least one selected from the group consisting of beta-glycyrrhizic acid, glycyrrhizic acid derivatives, aprene, aminocaproic acid, hydrocortisone, beta-glucan, licorice and mixtures thereof.

In the active principle, the acne treatment agent may include at least one selected from the group consisting of estradiol, estrogen, ethinyl estradiol, triclosan, azelaic acid and mixtures thereof.

In the active principle, the disinfecting agent may include at least one selected from the group consisting of benzalkonium chloride, benzethonium chloride, halocarbon and mixtures thereof.

In the active principle, the female hormone agent may be estrogen, and the estrogen may be at least one of estradiol, ethinyl estradiol, and isoflavone, which is a phytoestrogen.

In the active principle, the keratolytic agent may include at least one selected from the group consisting of sulfur, salicylic acid, AHA, BHA, resorcin and mixtures thereof.

In the active principle, the natural extract may include extracts of animals and plants, marine animals and plants or seaweed, or components obtained therefrom (functional ingredients having effects such as moisturizing, hydrating, pore-tightening, trouble reduction, whitening, elasticity restoration, wrinkle prevention, etc.).

Specifically, the natural extract may include at least one selected from the group consisting of *Hamamelis japonica, Lamium album, Mucuna, Pinus*, licorice, aloe, chamomile, rosehip, hinokitiol, horse chestnut, beta-carotene, ginseng extract, *Luffa aegyptiaca*, cucumber, layer extract, brown seaweed extract, *Dioscorea polystachya*, birch sap and mixtures thereof.

Also, the natural extract may include at least one selected from the group consisting of *Ascophyllum nodosum* extract, Iceland Alps glacier water, deep sea microorganisms, Antarctic microorganisms, *Mourera fluviatilis* extract, Arctic yeast, Arctic brown algae, sea parsley (Dulse), *Picea abies* (Nidiformis) extract and mixtures thereof.

In the cosmetic composition having increased skin contact and makeup persistence and the method of manufacturing the same according to embodiments of the present invention, skin contact and makeup persistence can be increased due to the use of a formulation surface-treated with a modified silicone film-forming agent, and moreover, powder dispersibility can be improved, thus making it possible to provide a superior use sensation to a user and to maintain high-quality makeup for a long time by overcoming problems in which the makeup effect does not last long.

Although the preferred embodiments of the present invention have been disclosed for illustrative purposes, those skilled in the art will appreciate that various modifications, additions and substitutions are possible without departing from the scope and spirit of the invention as disclosed in the accompanying claims. Therefore, all modifications and the like basically including the elements in the claims of the present invention should be considered to be included in the technical scope of the present invention.

What is claimed is:

1. A method of manufacturing a cosmetic composition having increased skin contact and makeup persistence, comprising:
    forming a powder continuous phase by mixing a powder and a film-forming agent; and obtaining a cosmetic composition in which a surface of the powder is compounded with the film-forming agent by heating the powder continuous phase for a predetermined time, wherein the forming the powder continuous phase comprises:

forming a first powder continuous phase activated with a weakly acidic region by placing 90 wt % to 99.5 wt % of the powder in a reactor, followed by addition with a powder activation solvent with stirring at 300 rpm to 700 rpm; and forming a second powder continuous phase by adding the first powder continuous phase with 0.5 wt % to 10 wt % of the film-forming agent with stirring at 200 rpm to 400 rpm.

2. The method of claim 1, further comprising homogenizing the cosmetic composition through pulverization and filtration.

3. The method of claim 1, wherein the obtaining the cosmetic composition comprises performing heating at a reaction temperature of 60° C. to 120° C. for 0.5 hr to 24 hr.

4. The method of claim 2, wherein the homogenizing comprises performing pulverization using a pulverizer of 3HP or more and filtration with 20 to 100 mesh.

5. The method of claim 1, wherein the powder is at least one selected from the group consisting of talc, kaolin, mica, sericite, nylon-12, methyl methacrylate crosspolymer, polymethyl methacrylate, boron nitride, alumina, titanium dioxide, zinc oxide, iron oxide, silica, pearl, organic dye, lake pigment, organic pigment and mixtures thereof.

6. The method of claim 1, wherein the film-forming agent is at least one selected from the group consisting of acrylate/dimethicone copolymer, acrylate/stearyl acrylate/dimethicone methacrylate copolymer, acrylate/ethylhexyl acrylate/dimethicone methacrylate copolymer, trimethylsiloxysilicate/dimethiconol crosspolymer, and mixtures thereof.

* * * * *